(12) United States Patent
Jackson et al.

(10) Patent No.: US 10,512,856 B1
(45) Date of Patent: Dec. 24, 2019

(54) METHOD OF EXTRACTING ONE OR MORE CHEMICAL EXTRACTS FROM A PLANT PRODUCT

(71) Applicant: Gildrien Farm, LLC, Leicester, VT (US)

(72) Inventors: Andrew Peter Jackson, Weybridge, VT (US); Jeremy Adam Gildrien, Leicester, VT (US)

(73) Assignee: GILDRIEN FARM, LLC, Leicester, VT (US)

( * ) Notice: Subject to any disclaimer, the term of this patent is extended or adjusted under 35 U.S.C. 154(b) by 0 days.

(21) Appl. No.: 16/246,256

(22) Filed: Jan. 11, 2019

(51) Int. Cl.
| | |
|---|---|
| C07D 311/00 | (2006.01) |
| C11B 1/00 | (2006.01) |
| B01D 11/00 | (2006.01) |
| B01D 11/04 | (2006.01) |
| C11B 1/10 | (2006.01) |
| C07D 311/80 | (2006.01) |
| C11C 1/00 | (2006.01) |

(52) U.S. Cl.
CPC ........ *B01D 11/0492* (2013.01); *C07D 311/80* (2013.01); *C11B 1/10* (2013.01); *C11C 1/007* (2013.01)

(58) Field of Classification Search
CPC ..... C07D 311/80; B01D 11/0492; C11B 1/10; C11B 3/006
See application file for complete search history.

(56) References Cited

U.S. PATENT DOCUMENTS

| 8,784,905 B2 * | 7/2014 | Lin ..................... A61K 36/315 |
| | | 424/725 |
| 9,655,936 B2 | 5/2017 | Ruben et al. |
| 9,732,009 B2 | 8/2017 | Raber et al. |
| 9,808,494 B2 | 11/2017 | Barringer |
| 9,867,859 B2 | 1/2018 | Raderman |
| 9,937,218 B2 | 4/2018 | Towle |
| 9,950,275 B1 | 4/2018 | Ruben et al. |
| 10,059,684 B2 | 8/2018 | Changoer et al. |
| 2003/0017216 A1 | 1/2003 | Schmidt et al. |
| 2013/0079531 A1 | 3/2013 | Barringer |
| 2013/0251824 A1 | 9/2013 | Hospodor et al. |
| 2016/0287652 A1 | 10/2016 | Scott |
| 2016/0346339 A1 | 12/2016 | Finley et al. |

FOREIGN PATENT DOCUMENTS

| CA | 2859930 | 3/2016 |
| WO | 2016153347 | 9/2016 |
| WO | 2017026897 | 2/2017 |
| WO | 2018209425 | 11/2018 |

* cited by examiner

*Primary Examiner* — Sikarl A Witherspoon
(74) *Attorney, Agent, or Firm* — Caldwell Intellectual Property Law (57) ABSTRACT

Disclosed is a method for extracting one or more chemical extracts from a plant product. The chemical extracts are purified and extracted by first separating at least a phytochemical bearing part of a plant product from one or more other portions of the plant product. A carrier oil is then heated at a target temperature to be used as the vehicle for extraction and then mixed with the at least a phytochemical bearing part while the target temperature is maintained. The process may be streamlined by having heating and mixing occur in a press device. The mixed carrier oil and the at least a phytochemical bearing part are then passed through the press device to produce an oil mixture. At least a chemical extract may be extracted from the oil mixture, and in some cases may be further purified by evaporation and/or centrifugation.

26 Claims, 6 Drawing Sheets

METHOD OF EXTRACTING ONE OR MORE CHEMICAL EXTRACTS FROM A PLANT PRODUCT

FIELD OF THE INVENTION

The present invention generally relates to the field of plant chemistry and extraction. In particular, the present invention is directed to a method of extracting one or more chemical extracts from a plant product.

BACKGROUND

Chemical extracts derived from plants have beneficial effects on both humans and animals. For example, digoxin which comes from the foxglove plant has beneficial effects to strengthen heart muscle for those suffering from heart failure. Furthermore, paclitaxel which comes from the Pacific yew has been used for many years to treat many different types of cancers. In addition, terpenes extracted from plants have many different uses in fragrances, foods, and drugs. It can be difficult and expensive to extract, resulting in costly and inefficient practices for extraction of chemical extracts. This has hampered use of chemical extracts, as they are too time-consuming and require overly expensive equipment to extract.

SUMMARY OF THE DISCLOSURE

Aspects of the present disclosure are directed to plant chemistry and extraction. In an embodiment, a method of extracting one or more chemical extracts from a plant product includes separating at least a phytochemical bearing part of a plant product from one or more other portions of a plant product, heating a carrier oil to a target temperature, mixing the at least a phytochemical bearing part and the carrier oil at the target temperature, passing the at least a phytochemical bearing part and the carrier oil through a press device to produce an oil mixture while the press device maintains the target temperature, and extracting from the oil mixture at least a chemical extract.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to methods and systems for extracting one or more chemical extracts from a plant product. In an embodiment, a method of extracting one or more chemical extracts may apply constant heat to at least a plant product to extract one more chemical extracts; this may permit extraction without the use of chemical solvents. Heat may be applied to at least a plant product externally for example by a heating such as an electric oven and/or hot plate. Heat may also be applied by a press device, thereby saving the number of steps involved and reducing the amount of equipment necessary to perform the extraction. A press device may include for example a press such as an oil press, rosin press, and/or auger style press. In addition, mixing of at least a plant product and a carrier oil such as olive, palm, medium chain triglyceride, sunflower, coco butter, and/or Vitamin E oil may be done externally using mixing equipment and/or performed by a press device to further speed up the extraction and reduce the number of steps and equipment necessary. The method as described in more detail below can be used to produce a variety of chemical extracts including for example a cannabinoid such as cannabidiol (CBD), cannabidiol acid (CBDA), cannabigerol (CBG), tetrahydrocannabinol (THC), *calendula* oil, mint, basil, turmeric, ginger, Ashwagandha, *Echinacea* and/or terpenes.

Figure 1:
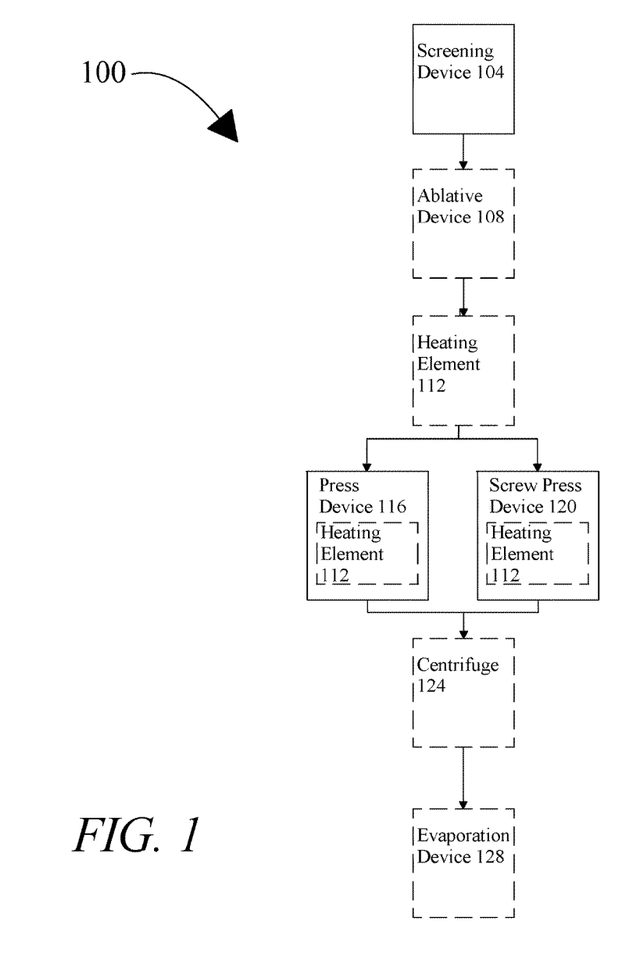
FIG. 1 is a block diagram of an exemplary embodiment of a system for extracting one or more chemical extracts from a plant product.

Referring now to the drawings, FIG. 1 illustrates an exemplary system 100 for extracting one or more chemical extracts from a plant product. System 100 includes screening device 104. A screening device 104 may include a device used to separate at least a part of a plant product from at least one or more other portions of the plant product. Plant product may include multicellular photosynthetic eukaryotes of the kingdom Plantae, as described in more detail below. As a non-limiting example, a screening device 104 may separate at least a phytochemical bearing part of a plant product from at least one or more other portions of the plant product. At least a phytochemical bearing part of a plant product may include portion of plant product from which a chemical extract may be extracted, including without limitation a portion from which the chemical extract is typically extracted. As used herein, at least a phytochemical bearing part may include leaves, flowers, rhizomes, roots, and/or stems of a plant. For example, a chemical extract containing mint may be extracted from phytochemical bearing part of a plant such as the leaves. In yet another example, a chemical extract containing turmeric may be extracted from phytochemical bearing part of a plant such as the rhizomes. In another embodiment, a chemical extract containing a cannabinoid may be extracted from phytochemical bearing part of a plant such as the flowers. Flowers as used herein are one or more reproductive parts of a plant product, such as for example the stamen, and/or the pistil as described below in more detail; as used herein, "flowers" may include any gametophyte-producing and/or spore-producing part of a plant, as well as the reproductive parts of angiosperms commonly referred to as "flowers." In yet another non-limiting example, a chemical extract containing *echinacea* may be extracted from phytochemical bearing part of a plant such as the roots.

Still referring to FIG. 1, a screening device 104 may include for example, a mesh sieve and/or a screening machine. A mesh sieve may contain specific sized openings so that that when the mesh and/or plant product are shaken or otherwise agitated, the mesh may allow pieces of the plant product that fit through the opening to pass through the mesh while larger particles of the plant product that do not fit through may be retained on the mesh. For example, plant product may be placed atop the mesh sieve and when shaken, at least a phytochemical bearing part of the plant product may pass through the mesh sieve while stem, seeds, and/or roots of the plant product may be retained on the mesh sieve. The size of the plant product that is allowed through the mesh sieve may be based on the openings of the mesh sieve. A mesh sieve may be categorized based on the size of the mesh sieve. For example, a size 16 sieve may have 16 openings per linear inch. In an embodiment, mesh sieve size may be selected based upon at least a phytochemical bearing part to be separated from a plant product. In such an instance, mesh sieve size may be selected based upon size of at least a phytochemical bearing part and other plant product parts will need to be selected and separated and need to fit through openings of mesh sieve and/or be held back and not fit through openings of mesh sieve. For example, when at least a chemical extract contains turmeric, a mesh sieve may be selected and utilized that will allow certain size material to fit through, but not allow larger material to pass through; rhizomes which may be larger than other parts of a plant product may not fit through a mesh sieve, but all other parts of a plant product may pass through. Continuing the above example, rhizomes containing phytochemical bearing part of turmeric may then be collected from atop the mesh sieve and used to extract at least a chemical extract containing turmeric. In yet another example, a mesh sieve may be selected that may only allow small phytochemical bearing parts of a plant product to pass through. For example, when at least a chemical extract contains cannabinoids, mesh sieve may contain openings that allow at least a flower part of a plant product to pass through, but other parts such as rhizomes, leaves, and/or stems may not pass through. At least a flower part of a plant product containing phytochemical bearing part of cannabinoids may then be collected and used to extract a cannabinoid for example.

Continuing to refer to FIG. 1, screening device 104 may also include a screening machine, which may take one material and separate it into multiple grades by particle size. For example, a plant product may be separated into multiple grades by particle size which may include a grade of the at least a phytochemical bearing part, a seed grade, and/or a root grade. A screening machine may include a drive that induces a vibration to physically separate material, a screen media that causes physical separation of the material, and a deck that holds the screen media and the drive and may be the mode of transport for the vibration. A screening machine may include circle-throw vibrating equipment which includes an eccentric shaft that causes a frame of a shaker to lurch at a given angle; the lurching action may propel material forward and up, and as the machine returns to its base state the material may fall by gravity to a physically lower level. A circle-throw vibrating machine may be composed of a shaker or series of shakers where drive causes a whole structure of the vibrating machine to move. The structure may extend to a maximum throw or length and then contract to a base state. A pattern of springs may be situated below the structure to perform vibration and shock absorption as the structure returns to a base state. A screening machine may include a screen cloth, which may be made of a material with specific size openings that allow specific size material to pass through the material whereas other material that cannot fit through the openings may be caught on the screen cloth. A screening machine may also include high frequency vibrating equipment, whereby a screen cloth vibrates and throws material on and off the screen cloth to allow particles of a certain size to cascade down the screen cloth. A screening machine may also include gyratory equipment whereby the machine may gyrate in a circular motion at a near level plane at low angles. A drive on gyratory equipment may include an eccentric gear box and/or eccentric weight. Material may roll over the screen and fall with induction of gravity and directional shifts. Rubber balls and trays may provide an additional mechanical means to cause material to fall through; the balls may provide a throwing action for the material to find an open slot to fall through. A screening machine may also include trommel screens where material may be fed into a horizontal rotating drum with screen panels around the diameter of the drum; the trommel screen may include a rotating drum on a shallow angle with screen panels around the diameter of the drum. Feed material may sit at the bottom of the drum and as the drum rotates, it may come into contact with a clean screen. A clean screen may include a screen cloth that does not have material currently resting on it. Larger material may travel to the end of the drum as it may not pass through the screen while smaller material may pass through the screen into a compartment below.

With continued reference to FIG. 1, system 100 includes an ablative device 108. Ablative device 108 may include any device that physically divide at least a plant product into smaller pieces, either before or after screening as described above. Such processing may include chopping, grinding, crushing, and/or cutting at least a plant product to reduce the size of the at least a plant product. This may include for example, chopping the at least a phytochemical bearing part to reduce the size of the at least a phytochemical bearing part. Ablative device 108 may include a cutting tool such as a blade that may contain a flat cutting edge that may chop, crush, and/or grind at least a plant product into smaller pieces. A blade may include a flat cutting edge of a tool. In an embodiment, a blade may include a hand-held blade that is controlled by a user, and/or an electric blade that may contain or be driven by a motor. Ablative device 108 may alternatively or additionally include other elements such as grinding elements, burrs, or any other device suitable for grinding at least a plant product into smaller pieces. As a non-limiting example, ablative device 108 may reduce at least a plant product into a coarse consistency. A coarse consistency may include rough and/or thick particles of at least a phytochemical bearing part of a plant product that may be produced by grinding, crushing, and/or chopping the at least a phytochemical bearing part of a plant product. A coarse consistency may resemble the size and/or shape of tea leaves. Tea leaves may include Western Style fermented black leaf tea, that may have medium sized leaves approximately 0.7-1.2 millimeters long. Ablative device 108 may alternatively or additionally reduce at least a plant product into a fine powder. A fine powder may include fine particles of at least a phytochemical bearing part of a plant product that may be produced by grinding, crushing, and/or chopping the at least a phytochemical bearing part of a plant product. A fine powder may include very fine particles that my flow freely when shaken or tilted. Ablative device 108 may include handheld, electric power tools, and/or machine tools that may further process at least a plant product. As a non-limiting example presented for purposes of illustration, ablative device 108 may include a food processor. A food processor may include an electric motor driven appliance that may contain blades and/or disks to facilitate in reducing the size of a material. A disk may include disks with blades designed to shred and/or slice material. A food processor may include blades and/or disks that can be removed and switched between either a blade or a disk. Blades and/or disks may be used to blend, chop, dice, and slice a material. A food processor may contain a base which contains a motor; the motor may turn a vertical shaft. A container such as a bowl may sit around vertical shaft. Blades and/or disks may be attached to shaft. A lid with a feed tube may be fitted onto the top of a bowl or pitcher incorporated in food processor; the feed tube may allow for material to be added to the food processor while it is chopping, grinding, and/or pureeing with the use of the blade and/or discs. Feed tube may also a plunger that may slide through the feed tube to allow material to be pushed down the feed tube; a hopper may alternatively or additionally be included in feed tube and/or food processor. As a further non-limiting example, ablative device 108 may include a mechanical grinding device such as a coffee or spice grinder; a coffee grinder, for instance, may include a motor attached to a blade that may rotate around a circular container. Circular container may include space where a material may be added. Circular container may include a top. When material is loaded into container blade may slice and/or tear the material to produce a fine powder. As an additional non-limiting example, ablative device 108 may include a blender. A blender may include a container with a rotating blade at the bottom, which may be powered by an electric motor located at the base of the blender; the container may have a lid to prevent material located in the container from spilling. Blade may include any of the blades as described above, and the blade may function to chop, grind, slice, and/or puree material located in the container. In an embodiment, a blender may include different speed settings that may control the speed of the blade as it rotates to chop, grind, slice, and/or puree material into different sizes. A blender may contain different controls and/or settings to control the speed of its blade.

With continued reference to FIG. 1, system 100 includes heating element 112. Heating element 112 may be any heating element that generates heat. Heating element 112 may include heating elements such as gas, oil, wood, coal, electric, solar, and/or geothermal sources of heat. Heating element 112 may include a resistive heating element. Resistive heating may include interactions between charge carriers such as electrons and the body of a conductor such as atomic ions, generating heat via electrical resistance when an electric current is applied. A voltage difference between two points of a conductor may create an electric field that may accelerate charge carriers in the direction of the electric field, giving them kinetic energy; when the charged particles collide with ions in the conductor, the particles may be scattered, and their direction of motion may become random rather than aligned with the electric field, which may constitute thermal motion. Energy from the electric field may be converted into thermal energy. Thermal energy may include energy that is transferred spontaneously from a hotter system or body to a colder system or body. Heat may include energy in transfer. Thermal energy may include internal energy which may include the internal energy of a system. An electric heating element may convert energy into heat through the process of resistive or Joule heating. Electric current passing through a heating element may encounter resistance resulting in heating of the heat element 112. Heating element 112 that includes electric sources of heat may include for example an electric stove. An electric stove may include an integrated electrical heating device that may contain at least a burner. Electric stove burners may be controlled by a rotary switch which may engage in different combinations of resistance and which may have a different heating power. An electric stove may include a thermostat. Heating element 112 may include a hot plate. A hot plate may contain a flat heated surface that may be portable. The heated surface may contain any suitable heating element as described above, including without limitation an electric heating element and/or a gas heating element such as a gas burner. Heating element 112 may include a gas stove which may use gas as a fuel source to generate heat. A gas stove may use gas fuel sources such as for example syngas, natural gas, propane, butane, liquefied petroleum gas and/or other flammable gas. Heating element 112 may include a microwave oven or similar device. A microwave oven may include an electric oven that generates heat by exposing it to electromagnetic radiation that may be within a certain frequency range. A microwave oven may generate non-ionizing electromagnetic radiation with a frequency that is higher than radio waves but lower than infrared light. In an embodiment, a microwave oven may utilize 2.5-1000-megahertz frequency. A microwave oven may include a high voltage power source such as a transformer which may pass energy to a magnetron. A magnetron which may convert high-voltage electric energy to microwave radiation. A magnetron may be connected to the high-voltage power source by a high voltage capacitor that may be connected to the magnetron. A microwave may include a magnetron control circuit, a metal cooking chamber, a turntable or metal wave guide stirring fan, and/or a control panel. Heating element 112 may include a vacuum oven. A vacuum oven may include an oven whereby moisture that may be present in a material such as a wet solid is removed by means of creating a vacuum. In an embodiment, a vacuum oven may include a vacuum dryer which may be composed of material such as cast iron, and/or stainless steel. A vacuum dryer may be divided into trays which may increase the surface area of the material for heat conduction. A vacuum oven door may be locked and connected to a vacuum pump to reduce the pressure inside the oven. Materials to be dried may be kept on trays inside the vacuum oven and pressure may be reduced by means of a vacuum pump. A vacuum oven door may be tightly shut, and steam may be passed through the space between trays so that heat may transfer by conduction. Heating element 112 may include an ultrasonic bath. Ultrasonic bath may utilize ultrasound waves to heat a fluid such as water. In an embodiment, a container may be filled with water. An ultrasound generating transducer may be built into the container or lowered into the fluid which may produce ultrasonic waves in the fluid such as water corresponding to an electrical signal oscillating at ultrasonic frequency. In an embodiment, ultrasonic waves may be generated between 20-400 kilohertz. A second container containing material to be heated may then be placed into the container containing the heated fluid, and heat may be transferred to the second container, thereby heating material contained within the second container. Heating element may include any other suitable bath, including without limitation hot water or fluid baths.

With continued reference to FIG. 1, system 100 includes a press device 116. Press device 116 may include a machine used to extract one or more chemical extracts from one or more materials using pressure; pressure may be greater than atmospheric pressure. A press device 116 may include for example, an oil press device, a rosin press device, and/or an auger type expeller extractor press device. A press device 116 may include heating element 112. In an embodiment, heating element 112 may be contained within, combined with, and/or attached to press device 116. Heating element 112 may include any of the heating elements as described above.

Figure 2:
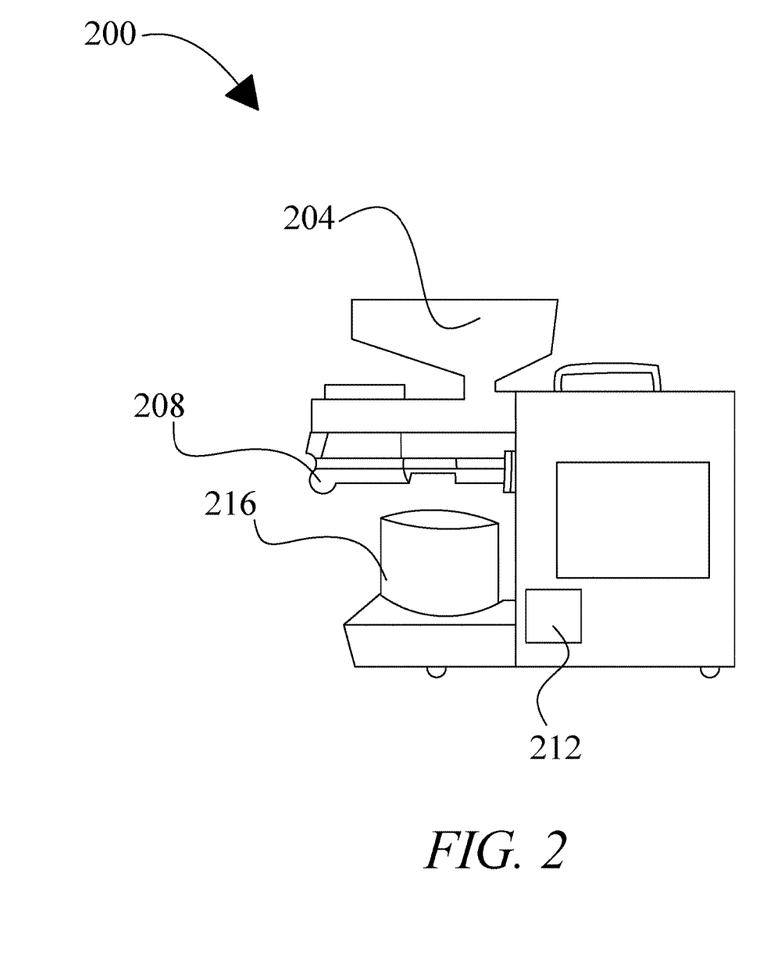
FIG. 2 is a schematic drawing of an exemplary embodiment of an oil press device.

Press device 116 may include, without limitation, an oil press device. Referring now to FIG. 2, a schematic drawing of an oil press device 200 is illustrated. An oil press device 200 may include an opening 204 through which a material may be added to the oil press device 200. In an embodiment, opening 204 may allow for material to be supplied in a continuous feed. The oil press device 200 may include a barrel 208 through which material may be passed and heated as part of the press device 116 process after being added to opening 204. The oil press device 200 may use friction and continuous pressure to move and compress device 116 material through barrel 208. The barrel may be of a certain size and shape and may include a heating element 112. In an embodiment, a barrel may be long and cylindrical in shape, through which a material can be laid out, dispersed, and heated evenly and continuously. In an embodiment, the barrel may be evenly heated and maintained at a target temperature, as determined by a user. Barrel 208 may include screw drives which may aid in moving and compressing material through barrel 208. A screw drive may include a rotating helical screw blade within barrel 208 that may move material through barrel 208. A screw drive may include of a trough or tube containing a spiral blade coiled around a shaft, that may be driven at one end and held at the other. The rate of volume transfer may be proportional to the rotation rate of the shaft. In an embodiment, a screw drive may be operated with the flow of material inclined upward. An oil press device 200 may contain an electric heating element 112 and may contain a user control panel 212 which may control the temperature of the heating element 112, barrel 208 and/or the time that the heat may be maintained for in heating element 112 and/or barrel 208. An oil press device 200 may contain an output collection container 216 whereby material that has passed through the oil press device 200 may be collected.

Figure 3:
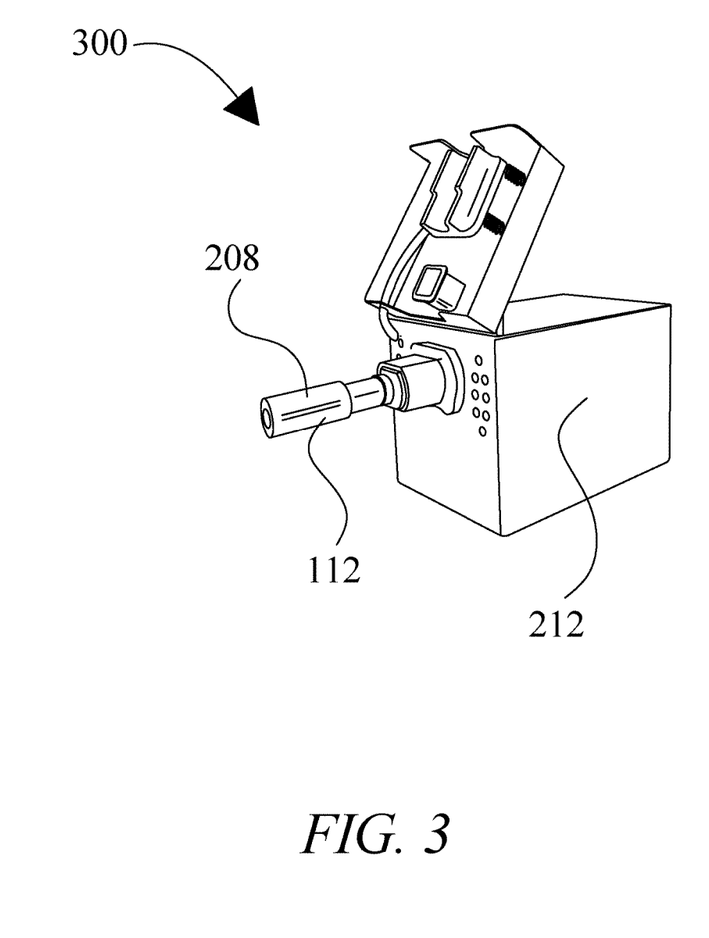
FIG. 3 is a schematic drawing of an exemplary embodiment of a side view of an oil press device.

Referring now to FIG. 3, a schematic drawing of a side view of an oil press device 300 is illustrated. Oil press device 300 may contain barrel 208. Barrel 208 may be long and cylindrical in shape, through which a material can be laid out, dispersed, and heated evenly and continuously. In an embodiment, the barrel 208 may be evenly heated and maintained at a target temperature, as determined by a user. Barrel 208 may be heated and maintained at a target temperature by heating element 112. Heating element 112 may be contained within barrel 208. Heating element 112 may be controlled by a user control panel 212 which may control the temperature of the heating element 112, barrel 208 and/or the time that the heat may be maintained for in heating element 112 and/or barrel 208.

Figure 4:
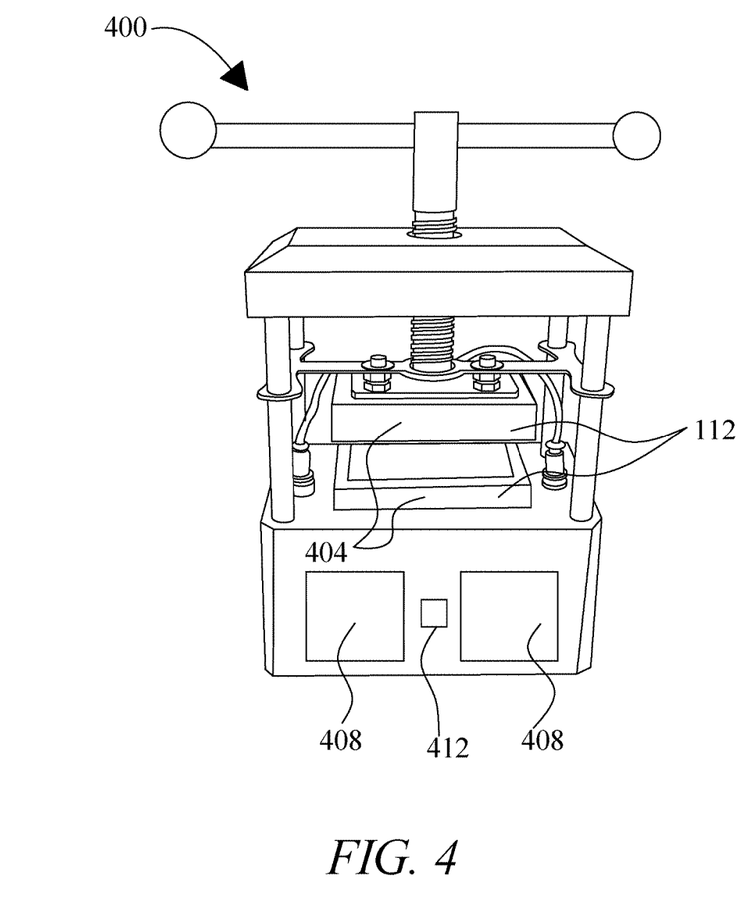
FIG. 4 is a schematic drawing of an exemplary embodiment of a rosin press device.

Press device 116 may include, without limitation, a rosin press device. Referring now to FIG. 4, a schematic drawing of a rosin press device 400 is illustrated. A rosin press device 400 may include a heating element 112 located within dual plates 404 that may allow for even heat distribution of material that may be added to rosin press device 400. In an embodiment, plates 404 may be made of aluminum material that conduct thermal heat to heat material that may be added on top of a plate, which may be a bottom plate, of plates 404. In an embodiment, material may be added to both plates or material may be added to one plate. Plates 404 may allow for even heat distribution as a material is laid down and spread out on a plate. Rosin press device 400 may include a control panel 408 which may include electric switches and programming that may allow the rosin press device 400 to be programmed to temperatures ranging from 0° to 415° Fahrenheit (−17.8° to 212.8° Celsius). Control panel 408 includes a timer that allows for pre-programmed heating of the rosin press device 400 and/or heating for a set period of time. In an embodiment, control panel 408 may include software control of heat being applied by each individual plate. In an embodiment, temperature may be adjusted to the top and/or bottom plate by taking into account readings from both plates and outside physical changes that may alter plate temperatures. Rosin press device 400 may include power switch 412 which may allow for rosin press device 400 to be turned on and off. Common examples of a rosin press device 400 that may be utilized include for example, ROSIN TECH TWIST as produced by Rosin Tech Products of Los Angeles, Calif., ROSIN TECH GO as produced by Rosin Tech Products of Los Angeles, Calif., ROSIN TECH SMASH as produced by Rosin Tech Products of Los Angeles, Calif., ROSIN TECH BIG SMASH as produced by Rosin Tech Products of Los Angeles, Calif., ROSIN TECH SQUASH as produced by Rosin Tech Products of Los Angeles, Calif., ROSIN TECH ALL-IN-ONE as produced by Rosin Tech Products of Los Angeles, Calif., ROSIN TECH PRO as produced by Rosin Tech Products of Los Angeles, Calif., ROSIN TECH PRO TOUCH as produced by Rosin Tech Products of Los Angeles, Calif., ROSIN TECH PRECISION ROSIN PRESS DEVICE as produced by Rosin Tech Products of Los Angeles, Calif., and/or ROSIN TECH ROLLER as produced by Rosin Tech Products of Los Angeles, Calif.

Referring back now to FIG. 1, a press device 116 may include an auger type expeller extractor press. An auger type expeller extractor may include a dewatering screw press that may separate liquids from solids. An auger type expeller extractor may include a screw press device 120 which may include a slow-moving device that dewaters by continuous gravitational drainage. A screw press device 120 may squeeze a material against a screen or filter and the liquid may be collected through the screen for collection and use. A screw press device 120 may include a shaft surrounded by a spiral steel plate, similar in design and appearance to a corkscrew. In an embodiment, a screw press device 120 may have dilute materials pumped directly into the screw press device 120. A screw press device 120 may be controlled by an electric motor. Compression may be created within the screw press device 120 by increasing the inner shaft diameter of the screw. A screw press device 120 may include an expeller which may remove water from fibrous material. A screw press device 120 may work by exerting extremely high pressure to for example convert fat in seeds into a liquid oil; by applying pressure and heat the oil may be liquefied and the flow through the screen may be collected. An example of a screw press device 120 may include a wine press device. In an embodiment, a screw press device 120 may include an electric control panel to control pressure and/or heat applied by the screw press device 120. Screw press device 120 may include a hopper or initial basket that the carrier oil may be placed into to be heated up by the screw press device 120. A user may then program screw press device 120 to be heated to the target temperature, for example. In an embodiment, the hopper may be of a specific size and length whereby the carrier oil can be spread out over a greater surface area to allow for continuous and even heating of the carrier oil. This may allow for heat to be applied more evenly to carrier oil as opposed to heating the carrier oil in a circular container such as a circular glass beaker, whereby more heat is applied at the bottom of the glass beaker that is in contact with the heating element. In an embodiment, heating element 112 may be contained within the entire length of screw press device 120. This may allow for heat to be more precisely controlled throughout the entire time that material is passed through screw press device 120. Any embodiment of system may alternatively or additionally include a hopper.

With continued reference to FIG. 1, system 100 may include a centrifuge 124. A centrifuge 124 may include machinery and/or equipment that may put a material in rotation around a fixed axis causing it to spin in a circle while applying a force perpendicular to the axis of spin. A centrifuge 124 may work using sedimentation principles whereby the circular outward rotation of the centrifuge causes denser substances and particles to move outward in a radial direction. Substances that are less dense may be displaced and move to the center. For example, a centrifuge 124 that uses test tubes to load a substance to be spun, may have denser particles settle to the bottom of the test tube while low-density substances may rise to the top. A centrifuge 124 may be characterized based on the speed in which a centrifuge may operate to be able to separate different particles. For example, a centrifuge 124 with a very high acceleration may be able to separate fine particles down to the nano-scale. Acceleration speed may be measured as revolutions per minute, which reflects how many times a centrifuge rotates in any given minute. Centrifuge 124 may include a continuous flow centrifuge which may allow for large volumes of material to be centrifuged without filling test tubes. Continuous flow centrifuge may contain a bucket-type container within which large volumes of material may be loaded altogether to be centrifuged. Continuous flow centrifuge may include SPINZALL CENTRIFUGE as produced by Booker and Dax Lab of New York, N.Y. In an embodiment, continuous flow centrifuge may rotate at a rate of 4100 revolutions per minute. Continuous flow centrifuge may include a pump that may allow it to be run continuously so that it may process one liter of material every twenty minutes. Continuous flow centrifuge may contain a mesh screen to further filter out impurities after material has been run through continuous flow centrifuge. For example, continuous flow centrifuge may contain an output pour that material may be collected from after spinning, and which then may be filtered through a mesh screen to further clarify and purify material. Mesh screen may contain a handle that may hang from output pour and allow material to flow through it and into a collection container. In an embodiment, a centrifuge may be utilized for a certain amount of time. A centrifuge may be used to clarify a material that is produced from the press device 116 for example. Clarification may include removing wax and free-floating pieces that may be found in a material. Wax may include for example material from the plant product that may be bound to the resin of the plant product. Resin may include a solid or highly viscous substance of plant. Plant resin may, as a non-limiting example, be secreted by a plant product as a protective measure in response to an injury. Plant resin may include terpenes, such as for example alpha-pinene, beta-pinene, delta-3 carene, sabinene, limonene, terpinolene, sesquiterpenes, longifolene, caryophyllene, delta-cadinene, and/or resin acids.

With continued reference to FIG. 1, system 100 may include an evaporation device 128. Evaporation device 128 may include any device capable of vaporizing at least a component of oil mixture as it changes into the gas phase when it reaches its boiling point. Evaporating may include for example boiling off any water remaining in a material to produce a material that includes substantially no water, or less than a selected threshold proportion of water. Evaporating a material such as an oil mixture may be performed by placing the oil mixture in a container, and heating the container containing the oil mixture to its boiling point. This may be done for example, by placing the container on a heating element 112 such as an electric stove and/or a hot plate as described in more detail above. A thermometer may be used to measure a temperature of a material to ensure that is reaches its boiling point and begins to vaporize. Temperature may be adjusted by a user as necessary.

Figure 5:
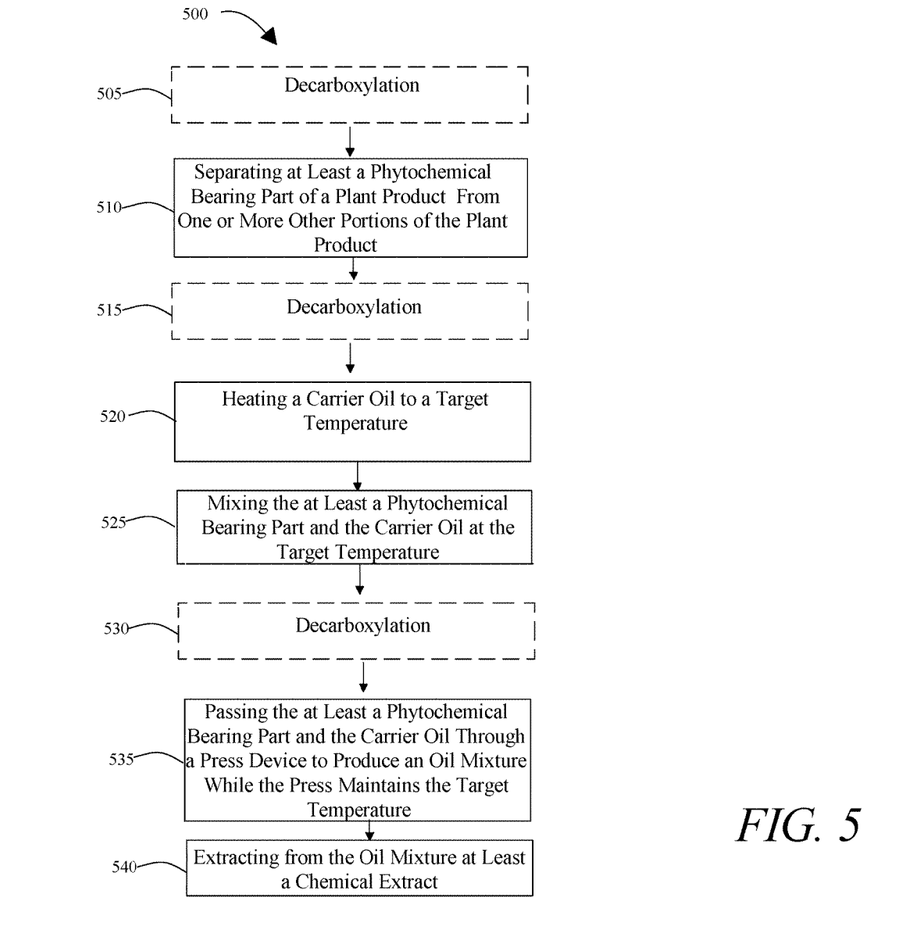
FIG. 5 is a block diagram of an exemplary embodiment of a method of extracting one or more chemical extracts from a plant product.

Referring now to FIG. 5, an exemplary embodiment of a method 500 of extracting one or more chemical extracts from a plant product is illustrated. At optional step 505 decarboxylation may be performed. At step 505, decarboxylation may occur to one or more plant products before at least a phytochemical bearing part of a plant product has been separated from one or more other portions of the plant product. Decarboxylation as used herein is a chemical reaction that removes a carboxyl group (COOH) and releases carbon dioxide (CO2). Decarboxylation may be performed by heating the at least a phytochemical bearing part and/or a plant product to a target temperature for a specific amount of time. Heating may be performed with the use of a heating element 112. For example, heating the at least a phytochemical bearing part to a target temperature may be performed by placing the at least a phytochemical bearing part in an oven, and/or on a heating element such as an electric stove or hot plate, as described in more detail above. In an embodiment, heating at least a phytochemical bearing part to the target temperature may be done in a vacuum oven. A vacuum oven may include a low-pressure oven that minimizes oxidation during drying. A vacuum oven may be programmed to reach the target temperature of 150° to 220° Fahrenheit (65.6° to 104.4° Celsius). Heat may be applied at a certain temperature and for a certain amount of time. In an embodiment, the plant product may be heated at a temperature between 150° to 220° Fahrenheit (65.6° to 104.4° Celsius) for 30-45 minutes. In an embodiment, decarboxylation may be optional, such as when decarboxylation may be performed at a later time, such as at optional step 515 and/or at optional step 530. In yet another embodiment, decarboxylation may be optional; for example, and without limitation, synthesis of the at least a chemical extract containing and/or consisting of cannabidiol acid (CBDA) may not need to be decarboxylated, either at step 505, step 515, and/or step 530. In yet another non-limiting example, synthesis of the at least a chemical extract including and/or consisting of *Calendula officinalis* may not require decarboxylation, either at step 505, step 515, and/or step 530. In an embodiment, decarboxylation may be optional and/or not required to produce at least a chemical extract.

With continued reference to FIG. 5, at step 510, at least a phytochemical bearing part of a plant product is separated from one or more other portions of the plant product. At least a phytochemical bearing part of a plant product may include one any port part described above as at least a phytochemical bearing part in reference to FIG. 1. In an embodiment, at least a phytochemical bearing part of a plant product may be separated from one or more other portions of the plant product such as for example a stem, seeds, and/or roots. In an embodiment, plant product may include one or more plant products from Cannabaceae family, including without limitation plant products belonging to *Asphananthe* genus, *Cannabis* genus, *Celtis* genus, *Chaetachme* genus, *Gironniera* genus, *Humulus* genus, *Lozanella* genus, *Parasponia* genus, *Pteroceltis* genus, and/or *Trema* genus. Plant product may include one or more plant products from the Asteraceae family, including without limitation *Calendula officinalis*. Plant product may include plants from the Lamiaceae family, Zingiberaceae family, and/or Solanaceae family. Plant product may include plants and/or plant products from *Mentha* genus, *Ocimum* genus, *Curcuma* genus, *Zingiber* genus, *Withania* genus, and/or *Echinacea* genus.

With continued reference to FIG. 5, separation may be performed utilizing a screening device 104. Screening device 104 may include any screening device 104 as described above in reference to FIG. 1, including, as a non-limiting example, a mesh sieve and/or a screening machine. A mesh sieve may contain specific-sized openings that when shaken, the mesh may allow pieces that fit through the opening through the mesh while larger particles that do not fit through may be retained on the mesh. For example, plant product may be placed atop the mesh sieve and when shaken, at least a phytochemical bearing part of the plant product may pass through the mesh sieve while stem, seeds, and/or roots of the plant product may be retained on the mesh sieve. Separation may alternatively or additionally include manual separation by a user who may be overseeing the separation process. For example, a user may physically separate by hand the at least a phytochemical bearing part of the plant product from the other parts of the plant product. For example, when separating portions of a plant product of *Cannabis Sativa*, at least a phytochemical bearing part of *Cannabis Sativa* may be picked by hand and separated from one or more other portions of *Cannabis Sativa* by a user. Separation may also include the use of a screening machine as described above, which may take one material and separate it into multiple grades by particle size. For example, a plant product may be separated into multiple grades by particle size which may include a grade of the at least a phytochemical bearing part, a seed grade, and/or a root grade.

With continued reference to FIG. 5, separating the at least a phytochemical bearing part of a plant product from one or more other portions of the plant product may include further processing of the at least a phytochemical bearing part through the use of an ablative device 108. Further processing may include chopping, and/or grinding the at least a phytochemical bearing part to a fine powder. Chopping may include crushing and/or cutting the at least a phytochemical bearing part to reduce the size of the at least a phytochemical bearing part. In an embodiment, chopping may be performed by a machine such as for example, a food processor. Grinding may include a cutting tool such as a blade, that may produce a very fine powder. For example, grinding may include use of powder tools and/or machine tools. In an embodiment, grinding may be performed by a coffee grinder and/or blender. For example, at least a phytochemical bearing part of a plant product may be placed in a coffee grinder wherein a blade and/or ablating element in the coffee grinder may slice and tear the at least a phytochemical bearing part of a plant product to produce a fine powder. A fine powder may include fine particles of at least a phytochemical bearing part of a plant product that may be produced by grinding, crushing, and/or chopping the at least a phytochemical bearing part of a plant product. A fine powder may include very fine particles that may flow freely when shaken or tilted.

With continued reference to FIG. 5, at optional step 515 decarboxylation may be performed. Decarboxylation may include any of the methods and/or steps of decarboxylation as described above in reference to step 505. Decarboxylation may occur to at least a phytochemical bearing part of a plant product that has been separated from one or more other portions of the plant product. Decarboxylation may be performed by heating the at least a phytochemical bearing part to a target temperature for a specific amount of time. Heating may be performed with the use of a heating element 112. For example, heating the at least a phytochemical bearing part to a target temperature may be performed by placing the at least a phytochemical bearing part in an oven, and/or on a heating element such as an electric stove or hot plate, as described in more detail above. In an embodiment, heating at least a phytochemical bearing part to the target temperature may be done in a vacuum oven. A vacuum oven may include a low-pressure oven that minimizes oxidation during drying. A vacuum oven may be programmed to reach the target temperature of 150° to 220° Fahrenheit (65.6° to 104.4° Celsius). Heat may be applied at a certain temperature and for a certain amount of time. In an embodiment, the at least a phytochemical bearing part may be heated at a temperature between 150° to 220° Fahrenheit (65.6° to 104.4° Celsius) for 30-45 minutes. In an embodiment, decarboxylation may be optional, such as when decarboxylation may be performed at a later time, such as at step 530. In yet another embodiment, decarboxylation may be optional; for example, and without limitation, synthesis of the at least a chemical extract containing and/or consisting of cannabidiol acid (CBDA) may not need to be decarboxylated, either at step 505, step 515, and/or step 530. In yet another non-limiting example, synthesis of the at least a chemical extract including and/or consisting of *Calendula officinalis* may not require decarboxylation, either at step 505, step 515, and/or step 530. Decarboxylation may include any of the methods and/or steps as described above. In an embodiment, decarboxylation may be optional and/or not required as described above.

With continued reference to FIG. 5, at step 520 a carrier oil is heated to a target temperature. As used herein, a carrier oil includes any nonpolar chemical substance that may be viscous at a specific temperature. For example, a carrier oil may include olive oil which is liquid at ambient temperature. Ambient temperature may include room temperature, which may be around 70° Fahrenheit (21.1° Celsius). A carrier oil may include coconut oil which is liquid at 76° Fahrenheit (24.4° Celsius). Carrier oil may include for example, olive oil, medium chain triglyceride oil, palm oil, coco butter, Vitamin E oil, sunflower oil, safflower oil, canola oil, hemp oil, apricot oil, and/or coconut oil. Carrier oil may be heated to a target temperature of 150° to 220° Fahrenheit (65.6° to 104.4° Celsius). Ratio by weight and/or mass of carrier oil that may be heated to at least a phytochemical bearing part may be between 0.5:1 and up to 2:1; so that 0.5 parts of carrier oil may be used to 1 part of the at least a phytochemical bearing part of a plant product and 2:1, so that 2 parts of carrier oil to 1 part of the at least a phytochemical bearing part of a plant product may be utilized. For example, 5 kilograms of the carrier oil may be heated to the target temperature whereby 10 kilograms of the at least a phytochemical bearing part of a plant product may have been separated from the plant product may be added in a 0.5:1 ratio. In yet another non-limiting example, 10 kilograms of the carrier oil may be heated to the target temperature whereby 5 kilograms of the at least a phytochemical bearing part of a plant product may have been separated from the plant product may be added in a 2:1 ratio. The carrier oil may be heated to the target temperature by a heating element 112, which may include any of the heating elements 112 as described in more detail above in reference to FIG. 1. For instance, and without limitation, heating element 112 may include an electric heating appliance that generates heat, gas, oil, wood, coal, solar, and/or geothermal sources of heat. In an embodiment, heating element 112 may be programmed to attain the target temperature between 150° to 220° Fahrenheit (65.6° to 104.4° Celsius). Heating element 112 may include for example an electric stove which may include an integrated electrical heating device that may contain at least a burner. Electric stove burners may be controlled by a rotary switch which may engage in different combinations of resistance and which may have a different heating power. An electric stove may include a thermostat. Heating element 112 may include a hot plate, which may include one or more electric heating elements or gas burners. In an embodiment, the carrier oil may be heated to the target temperature by a press device 116. A press device 116 may include a machine used to extract one or more chemical extracts from one or more materials using pressure. A press device 116 may include for example, an oil press device, a rosin press device 4, and/or an auger type expeller extractor such as for example, screw press device, for instance as described above in reference to FIGS. 2-4. In an embodiment, the carrier oil may be heated by an oil press device such as oil press device 200 as described above in reference to FIG. 2. In an embodiment, carrier oil may be added to oil press device 200 at 204. The carrier oil may then be heated in barrel 208 by at least a heating element 112 contained within barrel 208. In an embodiment, barrel 208 may be long and cylindrical in shape to allow the carrier oil to be evenly dispersed within barrel 208 and allow the carrier oil to be evenly heated. Control panel 212 may allow a user to program the oil press device 200 to attain the target temperature between 150° to 220° Fahrenheit (65.6° to 104.4° Celsius), for example, and for a set duration of time. For example, oil press device 200 may be programmed to the target temperature and for the duration that the carrier oil is processed through oil press device 200. In an embodiment, the carrier oil may be heated by a rosin press device 400, such as the one depicted in FIG. 4. In an embodiment, the carrier oil may be placed on plates 404 which may contain heating element 112. In an embodiment, the carrier oil may be spread out on plates 404 to allow the carrier oil to be evenly dispersed on plates 404 and allow the carrier oil to be evenly heated. Control panel 408 may allow a user to program the rosin press device 400 to attain the target temperature between 150° to 220° Fahrenheit (65.6° to 104.4° Celsius), and for a set duration of time. In yet another non-limiting example, the carrier oil may be heated by press device 116 such as screw press device 120. In an embodiment, heating carrier oil to target temperature between 150° to 220° Fahrenheit (65.6° to 104.4° Celsius) may include heating carrier oil above the target temperature. For example, carrier oil may be heated above target temperature to a temperature that takes into account the displacement of temperature when at least a phytochemical bearing part of a plant product may be added, so that upon addition of at least a phytochemical bearing part of a plant product to carrier oil target temperature is achieved.

With continued reference to FIG. 5, at step 525 the at least a phytochemical bearing part and the carrier oil are mixed at the target temperature. Mixing may include combining or putting together the at least a phytochemical bearing part and the carrier oil to form one substance. In an embodiment, mixing may be performed by adding the at least a phytochemical bearing part to the carrier oil while maintaining a target temperature and/or target temperature range. In an embodiment, the target temperature range may be 150° to 220° Fahrenheit (65.6° to 104.4° Celsius). In an embodiment, this may involve reheating carrier oil and at least a phytochemical bearing part back to the target temperature after the at least a phytochemical bearing part has been added to the carrier oil. At least a phytochemical bearing part may be added to carrier oil in press device 116. At least a phytochemical bearing part and carrier oil may then be maintained at a target temperature by press device 116. In an embodiment, at least a phytochemical bearing part and carrier oil may be mixed outside of press device 116, such as for example in a container over a heating element 112. For example, at least a phytochemical bearing part and carrier oil may be heated over a heating element 112 such as an electric stove in a container, which may include a container within press device 116, a glass container over or attached to a heating element, and/or any other suitable container and at least a phytochemical bearing part may be added to the container. In an embodiment, mixing at least a phytochemical bearing part and the carrier oil at the target temperature may be performed before carrier oil is heated to a target temperature. For example, carrier oil and at least a phytochemical bearing part may be mixed and then heated to the target temperature range between 150° to 220° Fahrenheit (65.6° to 104.4° Celsius) together. As a further non-limiting example, at least a phytochemical bearing part and carrier oil may be heated over or at a heating element 112 such as an electric stove in a container, and at least a phytochemical bearing part may be added to the glass container; a magnetic stirrer may then be added to container to assist in incorporating the at least a phytochemical bearing part into carrier oil. In an embodiment, at least a phytochemical bearing part and carrier oil may be heated using a heating element 112 such as an ultrasonic bath. At least a phytochemical bearing part and carrier oil may be mixed, before, during, and/or after heating, in container while maintaining a target temperature. Mixing may also include stirring the at least a phytochemical bearing part and the carrier oil. Stirring may be performed manually or stirring may be performed automatically such as for example with the use of a magnetic stirrer. A magnetic stirrer may include a device that employs a rotating magnetic field to cause a stir bar immersed in the carrier oil to spin, thus stirring it. Mixing may also be performed by press device 116 when at least a phytochemical bearing part is added to carrier oil in the press device 116. In an embodiment, press device 116 may contain a mixing button that may allow for continuous mixing to incorporate at least a phytochemical bearing part into carrier oil. In an embodiment, a target temperature may be maintained by placing a thermometer in at least a phytochemical bearing part and carrier oil mixture to see if a target temperature has been reached and maintained at different stages in the mixing process. In an embodiment, this may be done automatically when mixing occurs in press device 116 for example, which may include a temperature gauge of its own.

With continued reference to FIG. 5, after at least a phytochemical bearing part and carrier oil have been mixed, the resulting product may be decarboxylated at optional step 530. Decarboxylation may include removal of a carboxyl group (COOH) and release of carbon dioxide ($CO_2$) as described in more detail above. In an embodiment, at least a phytochemical bearing part may be heated at a temperature between 150° to 220° Fahrenheit (65.6° to 104.4° Celsius) for 30-45 minutes. In an embodiment, decarboxylation after mixing may be optional, such as when decarboxylation may have been performed earlier, either at step 505 and/or at step 515. In yet another embodiment, decarboxylation may not be performed. For example, synthesis of the at least a chemical extract including and/or consisting of cannabidiol acid (CBDA) may not need to be decarboxylated, either at step 505, step 515, and/or at step 530. In yet another non-limiting example, synthesis of the at least a chemical extract including and/or consisting of *Calendula officinalis* may not require decarboxylation, either at step 505, step 515, and/or at step 530.

With continued reference toto FIG. 5, at step 535, at least a phytochemical bearing part and carrier oil are passed through a press device 116 to produce an oil mixture while the press device 116 maintains the target temperature. A press device 116 may include any press device 116 as introduced above, including without limitation a machine used to extract one or more chemical extracts from one or more materials as described above in more detail in FIG. 1. At least a phytochemical bearing part and carrier oil may enter the press device 116 on one side and the resulting oil mixture may exit from the other end. In an embodiment, the resulting oil mixture may exit and be collected as in FIG. 2 at an output collection container 216. Waste products such as accumulated solids that do not end up in a resulting oil mixture may be collected separately. At least a phytochemical bearing part and carrier oil may be passed through the press device 116 continuously at a constant rate. In an embodiment, at least a phytochemical bearing part and carrier oil may be added to press device 116 at a continuous rate such as for example, at a rate of 5 pounds of the at least a phytochemical bearing part and the carrier oil per hour. A user may continuously feed at least a phytochemical bearing part and carrier oil into press device 116 at opening 204 as depicted in FIG. 2 for example. In yet another example, a user may place at least a phytochemical bearing part and the carrier oil onto a rosin press device 400 at plates 404 for example. Passing at least a phytochemical bearing part and carrier oil through press device 116 may include programming the press device 116 to the target temperature and to the desired rate. For example, a rosin press device 400 may include a software component that allows for a user to program the rosin press device 400 to maintain the target temperature as well as the rate of passing at least a phytochemical bearing part and carrier oil through the press device 116. In an embodiment, press device 116 and at least a phytochemical bearing part and carrier oil are maintained at the target temperature for the duration processing through the press device 116. This may enable at least a phytochemical bearing part and carrier oil to be maintained at target temperature and to not be cooled down during the entire processing through the press device 116. As at least a phytochemical bearing part and carrier oil are passed through the press device 116, a resulting oil mixture may seed through small openings that may not allow solids to pass through; the resulting oil mixture may be collected at one end of the press device 116 and the solids that did not pass through to form the resulting oil mixture may be removed from the press device 116 at another collection point. In an embodiment, a press device 116 such as an oil press device 200 may use friction and continuous pressure from screw drives while maintaining the target temperature to move and separate the resulting oil mixture from the solids that do not pass through openings. In an embodiment, pressure involved in processing an oil press device 200 may generate heat necessary to maintain the target temperature through the entire press device 116 process. In an embodiment, temperature may be continuously monitored and adjusted to ensure target temperature is maintained for the entire time that a press device 116 is operating and/or at least a phytochemical bearing part and carrier oil are passed through the press device 116. In an embodiment, a user who may be overseeing the process may stop and/or halt the press device 116 if the target temperature is not achieved and/or maintained.

With continued reference to FIG. 5, at step 540 at least a chemical extract is extracted from oil mixture. Extraction may include a separation process consisting of separating a chemical extract from oil mixture. For example, a chemical extract may be collected from an output 216 of an oil press device 200 and leftover material such as dissolved solutes may be discarded. A chemical extract may include a compound that has been purified from a plant product. A chemical extract may include for example, a cannabinoid. A cannabinoid may include a chemical compound that acts on cannabinoid receptors in organisms such as human beings and/or animals. A cannabinoid may include phytocannabinoids, endocannabinoids, and synthetic cannabinoids. Phytocannabinoids may include any of the more than 100 compounds found in plants, such as the plant *Cannabis Sativa*. Phytocannabinoids may occur in several other plant species in addition to *Cannabis Sativa*, which may include *Echinacea purpurea, Echinacea angustifolia, Acmella oleracea, Helichrysum umbraculigerum*, and/or *Radula marginata*. Phytocannabinoids may include cannabidiol (CBD), cannabidiol acid (CBDA), cannabidivarin (CBV), cannabigerol (CBG), tetrahydrocannabinol (THC), tetrahydrocannabinolic acid a (THCA), tetrahydrocannabivarin (THCV), cannabinol (CBN), cannabichromene (CBC), cannabicyclol (CBL), cannabivarin (CBV), cannabichromevarin (CBCV), cannabigerovarin (CBGV), cannabigerol monomethyl ether (CBGM), cannabielsoin (CBE), Delta-8 THC, Delta-9 THC, and/or Delta-9 THCA and/or cannabicitran (CBT). Endocannabinoids may include cannabinoids produced naturally in the body of organisms. Endocannabinoids may include endogenous lipid based retrograde neurotransmitters that may bind to cannabinoid receptors. Cannabinoid receptors may be located in the central nervous system and peripheral nervous system of mammals, for example. Cannabinoid receptors include both Cannabinoid receptor type 1 (CB1) and Cannabinoid receptor type 2 (CB2) type receptors, located within the central nervous system, peripheral nervous system, reproductive organism, skin, immune system, spleen, brain, cerebellum, medulla oblongata and digestive tract. Endocannabinoids include anandamide (AEA), 2-arachidonoylglycerol (2-AG), virodhamine, N-arachidonoyl dopamine (NADA), lysophosphatidylinositol (LPI) and noladin ether (2-arachidonyl glyceryl ether). Synthetic cannabinoids may be similar in structure to phytocannabinoids and/or endocannabinoids but may be synthesized instead of being naturally occurring such as in plants and/or in the human beings or animals. Synthetic cannabinoids may include for example, nonclassical cannabinoids such as cannabimimetics which may include the aminoalkylindoles, 1,5-diarylpyrazoles, quinolines, and arylsulfonamides as well as eicosanoids. At least a chemical extract may include a cannabinoid including phytocannabinoids, endocannabinoids, and synthetic cannabinoids. At least a chemical extract may include any of the precursors, metabolites, intermediates, degradations and/or chemicals necessary to produce and or synthesize any cannabinoids. For example, at least a chemical extract may include CBN, which is the primary product of THC degradation. In yet another non-limiting example, at least a chemical extract may include CBGA, which may be independently converted to either CBG, THCA, CBDA, and/or CBCA. At least a chemical extract may include *Calendula officinalis*. At least a chemical extract may include terpenes. Terpenes may include aromatic metabolites found in the oils of plants. Terpenes may include for example, alpha-pinene, beta-pinene, delta-3 carene, sabinene, limonene, terpinolene, sesquiterpenes, longifolene, caryophyllene, delta-cadinene, myrcene, humulene, linalool, caryophyllene, terpinolene, and/or resin acids. At least a chemical extract may include chemical extracts from leaves such as mint and basil; rhizomes such as turmeric and ginger; and roots such as Ashwagandha and *Echinacea*.

With continued reference to FIG. 5, extracting may include adding oil mixture to a centrifuge 124. A centrifuge 124 may include machinery and/or equipment that may put a substance such as the oil mixture in rotation around a fixed axis causing it to spin in a circle while applying a force perpendicular to the axis of spin. A centrifuge may work using sedimentation principles whereby the circular outward rotation of the centrifuge 124 causes denser substances and particles to move outward in a radial direction. Substances that are less dense may be displaced and move to the center. For example, a centrifuge 124 that uses test tubes to load a substance to be spun, may have denser particles settle to the bottom of the test tube while low-density substances may rise to the top. A centrifuge 124 may be characterized based on the speed in which a centrifuge may operate to be able to separate different particles. For example, a centrifuge with a very high acceleration may be able to separate fine particles down to the nano-scale. Acceleration speed may be measured as revolutions per minute, which may reflect how many times a centrifuge rotates in any given minute. In an embodiment, a centrifuge 124 may be utilized for a certain amount of time. For example, oil mixture may be added to a centrifuge and spun for twenty minutes. A centrifuge 124 may be used to clarify oil mixture that is produced from the press device 116. Clarification may include removing wax and free-floating pieces that may be found in oil mixture. Wax may include material from plant product that may be bound to resin of the plant product. Resin may include a solid or highly viscous substance of plant. As further disclosed above, plant resin may include terpenes, such as for example alpha-pinene, beta-pinene, delta-3 carene, sabinene, limonene, terpinolene, sesquiterpenes, longifolene, caryophyllene, delta-cadinene, and/or resin acids. In an embodiment, oil mixture may be added to a test tube in the centrifuge to clarify the oil mixture, and after being spun for a set period of time, the result may be that denser wax substances and left over plant resin may be present at the bottom of the test tube and the less dense oil mixture may be located at the top of the test tube. In an embodiment, centrifuge 124 may be maintained at the target temperature; for instance, and without limitation, the centrifuge 124 may contain a temperature control that may allow a user to program the temperature that the centrifuge maintain while the oil mixture is spun. For example, a user may program a centrifuge 124 to maintain the target temperature between 150° to 220° Fahrenheit (65.6° to 104.4° Celsius).

With continued reference to FIG. 5, extracting may include evaporating oil mixture. Evaporating oil mixture may include vaporizing one or more components the oil mixture as the one or more components change into the gas phase when the one or more components reach a boiling point. Evaporating may be performed using an evaporation device 128. An evaporation device 128 may include any of the equipment and/or devices as described above in more detail in FIG. 1. As a non-limiting example, evaporating may include boiling off any water remaining in oil mixture to produce an oil mixture that has been evaporated of water. Evaporating oil mixture may be performed by placing the oil mixture in a container, and heating the container containing the oil mixture to its boiling point. This may be done for example, by placing the container on a heating element 112 such as an electric stove and/or a hot plate as described in more detail above. A thermometer may be used to measure a temperature of oil mixture to ensure that is reaches its boiling point and begins to vaporize. Temperature may be adjusted by a user as necessary. A resulting oil mixture that may be left after evaporating may include at least a chemical compound which may include terpenes. Terpenes may include any of the substances as described above in more detail. Evaporating oil mixture to produce at least a chemical extract such as a terpene may be a non-solvent based terpene extraction. At least a chemical extract such as a terpene may be produced through evaporation and without the addition of any solvents to the oil mixture. As the oil mixture is heated, the lighter oils which may include certain classes of terpenes may be drawn out of the oil mixture and float on the surface to be easily collected. In an embodiment, evaporating may be done in conjunction with centrifugation. For example, oil mixture may be centrifuged followed by evaporating. In yet another non-limiting example, oil mixture may be evaporated followed by adding the oil mixture to a centrifuge. In yet another non-limiting example, oil mixture may only be centrifuged, the oil mixture may only be evaporated, and/or the oil mixture may be neither evaporated or centrifuged.

With continued reference to FIG. 5, terpene extraction may include a solvent based extraction. In an embodiment, a solvent may be added to oil mixture to produce at least a chemical extract that contains terpenes. Terpenes may include any terpenes as described in more detail above. A solvent may include a compound that dissolves a solute. A solvent may include for example, butane, propane, butane hash, live resin, alcohol, and/or carbon dioxide ($CO_2$). In an embodiment, a solvent may be added to oil mixture to draw out terpenes from the oil mixture. For example, ethanol may be added to oil mixture, wherein ethanol has both polar and nonpolar ends which allows the ethanol to bond with a wide variety of molecules. Ethanol may bond with terpenes and allow the terpenes to be extracted. In an embodiment, oil mixture that may have a solvent added may be subject to centrifugation and/or evaporation. In yet another non-limiting example, oil mixture that may have a solvent added may not be subject to centrifugation and/or evaporation.

Figure 6:
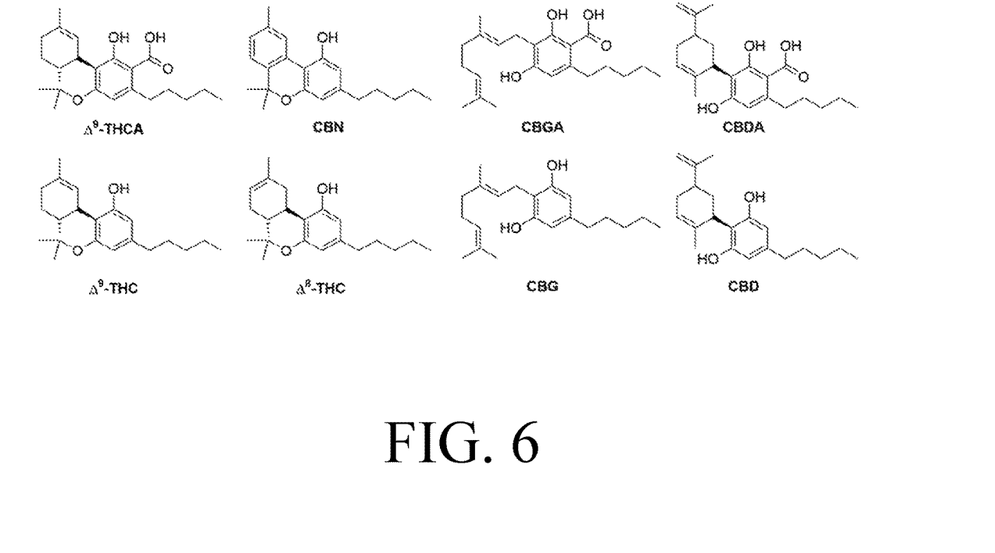
FIG. 6 is a table illustrating diagrams of chemical extracts.

Referring now to FIG. 6, a table of at least a chemical extract is illustrated. At least a chemical extract may include a cannabinoid. A cannabinoid may include for example, a chemical extract such as CBDA, CBGA, CBD, CBG, CBN, Delta-8 THC, Delta-9 THC, and/or Delta-9 THCA as illustrated in FIG. 6.

Embodiments of the disclosed method may have several advantageous over other methods of extraction; in an embodiment, methods disclosed herein allow for extraction of at least a chemical extract from a plant product without the use of many solvents and/or other chemicals that need to be added. In an embodiment, no chemical solvents may be needed, with the unexpected benefit that heat alone may be used to extract at least a chemical extract. In yet another embodiment, many chemical solvents may not be needed to extract at least a chemical extract from a plant product, as contrasted with previously existent methods. In an embodiment, decarboxylation of plant products may not need to occur at all. In an embodiment, decarboxylation of plant products may be optional. In an embodiment, maintaining and applying constant heat during the extraction process may be all that is necessary to extract at least a chemical extract from a plant product. Methods disclosed herein may use inexpensive equipment that may be commonly found and available. In addition, embodiments of methods may allow for many steps to be performed at once by heating and/or mixing in a press device; this may allow for time to be saved and reduce the amount of equipment that may be necessary to perform the method.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of extracting one or more chemical extracts from a plant product, the method comprising:
   separating at least a phytochemical bearing part of a plant product from one or more other portions of the plant product;
   heating a carrier oil to a target temperature;
   mixing the at least a phytochemical bearing part and the carrier oil at the target temperature;
   passing the at least a phytochemical bearing part and the carrier oil through a press device to produce an oil mixture while the press device maintains the target temperature; and
   extracting from the oil mixture at least a chemical extract;
   wherein heating the carrier oil to the target temperature is performed by a heating element located within the press device.

2. The method of claim 1, wherein separating further comprises separating using a sieve.

3. The method of claim 1, wherein separating further comprises grinding the at least a phytochemical bearing part to a coarse consistency.

4. The method of claim 1, wherein heating further comprises heating to a temperature between 150° Fahrenheit and 220° Fahrenheit.

5. The method of claim 1, wherein the carrier oil further comprises an oil that is liquid at a temperature between 150° Fahrenheit and 220° Fahrenheit.

6. The method of claim 5, wherein the carrier oil further comprises olive oil.

7. The method of claim 5, wherein the carrier oil further comprises a medium chain triglyceride oil.

8. The method of claim 5, wherein the carrier oil further comprises palm oil.

9. The method of claim 5, wherein the carrier oil further comprises coco butter.

10. The method of claim 5, wherein the carrier oil further comprises Vitamin E oil.

11. The method of claim 5, wherein the carrier oil further comprises sunflower oil.

12. The method of claim 5, wherein the carrier oil further comprises apricot oil.

13. The method of claim 5, wherein the carrier oil further comprises hemp oil.

14. The method of claim 1, wherein heating the carrier oil to the target temperature further comprises evenly applying heat to a surface area of the carrier oil.

15. The method of claim 1, wherein:
   the at least a phytochemical bearing part and the carrier oil have a surface area when combined; and
   the press device evenly applies heat to the surface area of the at least a phytochemical bearing part and the carrier oil.

16. The method of claim 1, wherein the press device further comprises an oil press device.

17. The method of claim 1, wherein the press device further comprises a rosin press device.

18. The method of claim 1, wherein extracting further comprises adding the oil mixture to a centrifuge.

19. The method of claim 18, wherein the centrifuge is maintained at the target temperature.

20. The method of claim 1, wherein extracting further comprises evaporating the oil mixture.

21. The method of claim 1, wherein the chemical extract further comprises a cannabinoid.

22. The method of claim 1, wherein the chemical extract further comprises *calendula* oil.

23. The method of claim 1, wherein the chemical extract further comprises terpene.

24. The method of claim 1 further comprising decarboxylating the at least a plant product.

25. The method of claim 1 further comprising decarboxylating the at least a phytochemical bearing part of the plant product.

26. The method of claim 1 further comprising decarboxylating the at least a phytochemical bearing part of the plant product and the carrier oil.

* * * * *